United States Patent [19]

Mannheimer

[11] Patent Number: 5,782,756
[45] Date of Patent: Jul. 21, 1998

[54] METHOD AND APPARATUS FOR IN VIVO BLOOD CONSTITUENT ANALYSIS

[75] Inventor: Paul D. Mannheimer, Danville, Calif.

[73] Assignee: Nellcor Puritan Bennett Incorporated, Pleasanton, Calif.

[21] Appl. No.: 715,848

[22] Filed: Sep. 19, 1996

[51] Int. Cl.⁶ .......................................... A61B 5/00
[52] U.S. Cl. ........................ 600/322; 600/323; 600/336
[58] Field of Search ............................. 128/633, 664, 128/665, 666; 356/41; 600/322, 323, 326, 328, 330, 336, 473, 476, 479

[56] References Cited

U.S. PATENT DOCUMENTS 5,645,060  7/1997  Yorkey .................................. 128/633

*Primary Examiner*—Jennifer Bahr
*Assistant Examiner*—Eric F. Winakus
*Attorney, Agent, or Firm*—Townsend and Townsend and Crew LLP

[57] ABSTRACT

The present invention utilizes at least three wavelengths of electromagnetic radiation for determining a blood constituent, such as arterial oxygen saturation, in a patient. The detected radiation scattered by the tissue of the patient is analyzed in a manner that compensates for variations in the detected radiation caused by differences in the scattering of the radiation at different wavelengths. In particular, a result is determined which is equivalent to the sum of a first blood constituent estimate using a first pair of the detected signals, and the difference between the first blood constituent estimate and a second blood constituent estimate, using a different pair of wavelengths, with the difference being multiplied by a multiplicative factor.

58 Claims, 4 Drawing Sheets

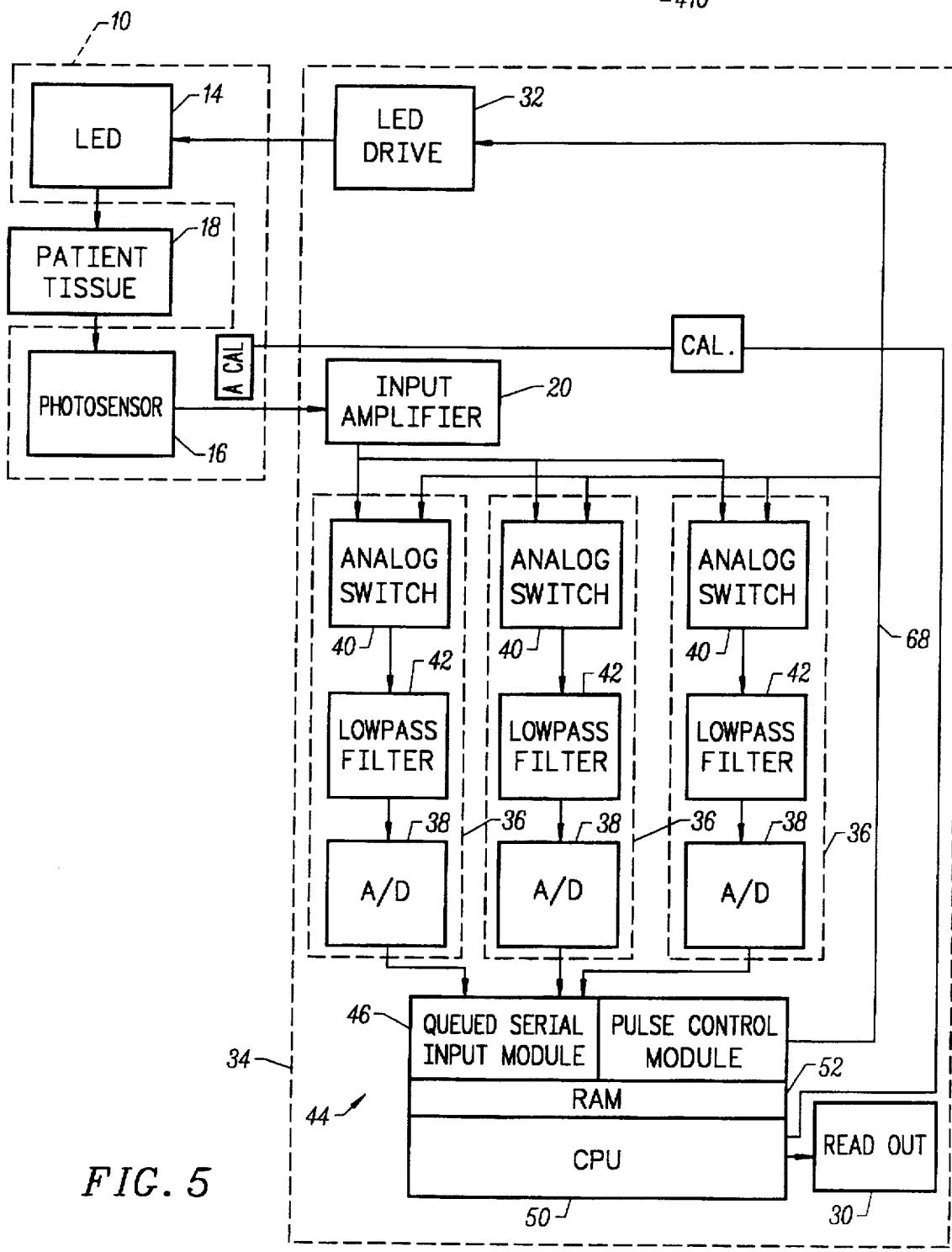

| Algorithm | Std. Dev. Error (0-60% SaO$_2$) | SpO$_2$ range @ 20% SaO$_2$ |
|---|---|---|
| 660/900 | 15.6 | 10%-48% |
| 735/900 | 6.6 | 15%-34% |
| improved | 2.9 | 21%-23% |

METHOD AND APPARATUS FOR IN VIVO BLOOD CONSTITUENT ANALYSIS

BACKGROUND OF THE INVENTION

The present invention relates to the use of at least three wavelengths in oximetry, and in particular to a method and apparatus for compensating for errors due to the differences in interaction of the radiation with the patient at different wavelengths.

Pulse oximetry can yield inaccurate estimates of the arterial blood oxygen saturation ($SaO_2$) when corrupting conditions are present such as motion, the presence of dysfunctional hemoglobins, or a variety of other tissue-based causes which primarily affect the accuracy of conventional approaches at low oxygen saturations. A three-or-more-wavelength sensor and algorithm will be described which are intended to be minimally sensitive to a variety of corrupting causes that produce their largest effects when saturations are less than 70%.

Pulse oximetry is used to monitor continuously the arterial blood oxygen saturation of adults, children and neonates in the operating room, recovery room, intensive care unit, and increasingly on the hospital's general floor. Patients encountered in these environments typically have saturation greater than 90% and rarely below 70%. When saturation does fall below the normal range, an unhealthy clinical condition is indicated and some form of intervention generally occurs. Here, limited accuracy at low saturation does not affect the clinical utility of the system.

Recently, the use of pulse oximetry has been expanded into the obstetrical delivery room where it is being used for monitoring the oxygen status of the fetus during labor and delivery. The range of normal saturations in the fetus is much lower, typically 20%–75%, and accuracy in the low saturation range takes on additional importance in assessing fetal well-being. As conventional oximeters tend to read less accurately at very low saturations, there is a need to create a pulse oximetry system that is clinically useful in this range.

The typical pulse oximetry sensor contains two LEDs that emit red (650–670 nm) and near infrared (850–940 nm) light into a pulsatile tissue bed. Light scattered by the tissue is collected with a photodiode positioned on an opposite surface (transmission pulse oximetry), or an adjacent surface (reflectance pulse oximetry.) The "pulse" comes from the time-varying amount of arterial blood in the tissue during the cardiac cycle. In a pulse oximeter, signals collected by the photodetector create a plethysmographic waveform due to the resulting cycling light attenuation. The relative modulation of the collected red and near infrared (IR) light signals, referred to as the modulation ratio "R," is used to estimate arterial oxygen saturation, $SpO_2$, based on an empirical calibration relationship expressed within the oximeter (the letter "p" indicates that the value comes from pulse oximetry.) Pulse oximeters differ from the earlier class of oximeters which will be described herein as "DC oximeters", in that DC oximeters make computational use only of the time-averaged light transmission through tissue.

It should be understood that in some oximeters the tissue whose optical properties are measured may simply be blood (as is the case with many invasive fiber optic catheter oximeters), while other oximeters measure the optical properties of solid tissues, such as skin, which are at least partially perfused with blood.

Pulse oximetry can yield inaccurate estimates of the arterial blood oxygen saturation ($SaO_2$) when corrupting conditions are present such as motion, the presence of dysfunctional hemoglobins, or a variety of other causes which primarily affect the accuracy of conventional pulse oximeters at low oxygen saturations. Many prior art variations on the methodology of pulse oximetry have been developed to minimize the occurrence of errors; however most base their fundamental algorithms on homogeneous tissue beds and generally follow a Beer's Law description of light absorption. Typically only two wavelengths are used in pulse oximetry, but in some circumstances three or more wavelengths are utilized to accommodate certain factors. The following list describes prior art three-wavelength techniques for determining blood oxygen saturation:

1) Barthelemy et al. (U.S. Pat. No. 5,413,100) use three wavelengths (660, 750, 940 nm) in a pulse oximeter to additionally measure the relative amount of carboxyhemoglobin (COHb) present in the arterial blood (a minimum of two wavelengths are required for $SpO_2$ determination.) Errors in the $SpO_2$ value result without such compensation in the presence of high concentrations of COHb.

2) Schmitt et al. (U.S. Pat. No. 5,040,539) utilize green, red, and near infrared light in a pulse oximeter to measure $SpO_2$ in a tooth. Signals from the additional green wavelength are subtracted from the red and IR signals to account for shunting through the non-blood-perfused portions of the tooth.

3) Hatschek (U.S. Pat. No. 5,299,570) utilizes similar wavelengths to those selected by Schmitt, but rather than using transmission of the extra wavelength to improve $SpO_2$ accuracy, he uses this extra information to permit estimation of the relative blood volume in the tissue.

4) Hamaguri et al. (U.S. Pat. No. 4,714,341) perform two simultaneous estimates of $SpO_2$ using three wavelengths (650, 710, 810 nm), and determine the validity of the estimates based on their agreement with one another. In the presence of motion, the two calculated $SpO_2$ values will be in sharp disagreement, while in the absence of motion their difference will be less than a specified threshold.

5) Three wavelength algorithms are commonly used in invasive fiber optic catheter DC oximeters for non-pulsatile determination of oxygen saturation in a large vessel (Shaw, U.S. Pat. Nos. 3,638,640; 4,114,604; Sperinde, U.S. Pat. No. 4,623,248.) The third wavelength is necessary to account for the hematocrit-dependent scattering effects of whole blood.

6) Multivariate techniques considering many wavelengths are suggested by the work from Sandia Labs (U.S. Pat. Nos. 5,355,880; 5,494,032; and EP 0522 674 A2.) Here, the many wavelengths are utilized to account for many constituents in the blood in a DC oximeter ('880) or used to minimize the effects of other interfering spectral absorbers and/or limited signal-to-noise in a pulse oximeter ('032 and the European application.)

7) Pologe (U.S. Pat. No. 5,297,548), like Hatschek, attempts to measure hemoglobin concentration by the use of a third wavelength, in this case 1270 nm, with a pulse oximeter. Pologe describes the importance of locating multiple emitters and multiple detectors close to one another in their respective apertures in order to ensure that the light paths at the multiple wavelengths are the same.

The prior art methods of items 1, 3, 5 and 6 are intended to make more accurate estimates of $SaO_2$ by accounting for the effects of light loss from constituents other than oxyhemoglobin and deoxyhemoglobin. The methods in items 2 and 4 are intended to accommodate for known limitations in pulse oximetry during conditions of shunting of the probing light or motion. Except for patent '539, each of these methods assumes that the blood is homogeneously distributed in the underlying tissue. Patent '539 describes the application of pulse oximetry in an extraordinary part of the body (the tooth) in which no blood is found in a portion of the tissue. Items 5 and part of 6 describe DC oximeters, as distinct from the pulse oximeters described in the present invention.

Pulsatile blood, however, is not necessarily homogeneously distributed in living tissues. Depending on sensor placement and the physiological state of the patient, $SpO_2$ readings can be inaccurate even in the absence of confounding chromophores such as COHb, variable blood volumes, or direct shunting of the sensor's emitted light by blood-free tissue. Mannheimer (U.S. Pat. No. 5,524,617) teaches the use of multiple emitter and/or detector locations to accommodate for the potential layering of tissues with different optical characteristics. Mannheimer and Chung (U.S. Pat. No. 5,218,962) place multiple emitter or detector pairs adjacent to one another in an effort to determine if readings are consistent from adjacent tissue regions. Casciani et al. (U.S. Pat. No. 5,421,329) recognize that not only is the blood potentially heterogeneously distributed within the tissue, but the probing light rays at the multiple wavelengths do not necessarily traverse the same tissues even if spatial separation of multiple emitters and potentially multiple detectors is eliminated. This is due to the fact that light absorption and scattering within the tissue bed is wavelength-dependent. Patent '329 teaches the utility of choosing sensor wavelengths based on matching of certain tissue properties in the saturation range of interest in order to best overlap detected light penetration. But as pointed out in the '329 patent, trade-offs are present which limit the choice of wavelengths and do not necessarily guarantee penetration overlap at the particular saturation of interest. The '617, '962, and '329 patents listed above describe computations utilizing only two emitter wavelengths for determining blood oxygen saturation.

It will be helpful in understanding the phenomena described herein to recognize that much of the light which leaves the sensor's light source goes into the patient's tissue and is absorbed without ever finding its way to the detector. The only light rays which affect the measurement are those which do reach the detector. The paths which these detected rays take are only a subset of the paths taken by all the light rays which enter the tissue. It is the spatial distribution of the paths of the detected rays which determines the relative importance of the different parts of an inhomogeneous tissue bed in determining the final measurement result. (This is discussed more fully in "Wavelength selection for fetal pulse oximetry," Mannheimer et al., accepted for publication in IEEE Trans Biomed Eng.

In order to more fully understand some of the causes of $SpO_2$ reading errors at low oxygen saturations, one must consider the regions of tissue probed by the detected light in a pulse oximetry sensor. As described in the '329 patent, the penetration depth (and/or breadth) of light in living tissue relates to the wavelength-dependent absorption and scattering characteristics of the tissue. When light sources peaked at 660 nm and 900 nm are used, the penetration depths are well matched at high $SaO_2$ levels. As the saturation drops, however, the detected red light comes primarily from only the shallow depths since the hemoglobin in the tissue preferentially absorbs the red photons which travel the longest distances. The detected IR light, on the other hand, has penetrated much deeper since at low saturation IR light is less strongly absorbed. If the two wavelengths of light travel into different depths or regions of tissue, the relative degree of signal pulsatility observed at the photodetector may no longer simply relate to the saturation of the pulsing blood. For example, if there are more-strongly-pulsatile blood vessels deep in the tissue than at shallow layers, deep-penetrating IR rays may experience stronger modulation, relative to that experienced by shallow-penetrating red rays, than would be predicted by assuming a uniform distribution of pulsatile blood in the tissue. Furthermore, perturbations to tissue parameters, such as vasoconstriction or exsanguination in the superficial layers, may not equally affect the pulsatile signals at the two wavelengths, and thus not "cancel" as is generally modeled using Beer's Law. As taught in '329, penetration depths at lower oxygen saturations are significantly better matched when 735 nm and 900 nm light is used, and consequently the same perturbations have much less influence. The penetration match is still not perfect over the full saturation range, however, and to a measurable degree $SpO_2$ can be affected by parameters other than $SaO_2$.

SUMMARY OF THE INVENTION

The present invention utilizes at least three wavelengths of electromagnetic radiation for determining a blood constituent, such as arterial oxygen saturation, in a patient. The detected radiation scattered by the tissue of the patient is analyzed in a manner that compensates for variations caused by differences in the scattering of the radiation at different wavelengths. In particular, a result is determined which is equivalent to the sum of a first saturation estimate using a first pair of the detected signals, and the difference between the first saturation estimate and a second saturation estimate, using a different pair of wavelengths, with the difference being multiplied by a multiplicative factor.

The method of the present invention compensates for differences in path length of radiation at different wavelengths which are affected by non-homogeneous tissue. The present invention is particularly useful for sites on a fetus, where the accessible sites typically have non-homogeneous tissue, and also where the fetus typically has an arterial oxygen saturation of less than 70%. The invention is also useful for adult oxygen saturation determination.

The present invention can be implemented using a number of different algorithms or coefficients as set forth in the following detailed description. In addition, the selection of the wavelengths utilized can be done in a manner to optimize performance of the oximeter for non-homogeneous tissue, in particular to optimize it for fetal tissue with arterial oxygen saturation of less than 70%. The wavelengths are chosen so that two different pairs of wavelengths of the three wavelengths meet two criteria. First, they should have sufficient sensitivity to changes in oxygen saturation so that, preferably, the ratio of detected intensity modulation varies by more than double between 0 and 100% saturation. Second, the two different pairs of wavelengths must have sufficiently different detected light penetrations into the patient tissue and also having sufficient overlap to provide correlated errors in saturation calculation.

A further understanding of the nature and advantages of the present invention may be realized by reference to the following description taken in conjunction with the accompanying drawings.

BRIEF DESCRIPTION OF THE DRAWINGS

FIG. 4 is a diagram of three emitters for emitting three wavelengths according to the invention;

FIG. 5 is a block diagram of an oximeter system which can be used with the present invention;

DETAILED DESCRIPTION OF THE PREFERRED EMBODIMENTS

Figure 1:
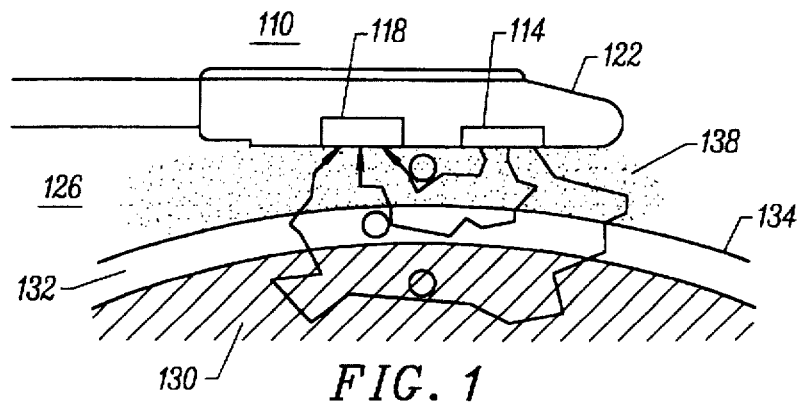
FIG. 1 is a diagram illustrating the difference in penetration of a tissue sample by different wavelengths of light.

FIG. 1 illustrates a problem addressed by the present invention. A fetal sensor probe 110 is shown having light emitters 114 and detector 118 mounted in housing 122. Three different light paths, 1, 2 and 3 illustrate different possible penetration depths for light of different wavelengths. The light paths pass through different layers, including a blood-perfused layer 130, a bloodless layer 132, and surface layer 138 which can include such things as hair, mucus, etc. between the probe and skin 134. Although the sensor shown in FIG. 1 is a reflectance oximeter sensor, a transmissive sensor would be subject to a similar effect, with the light spreading or scattering different amounts during transmission depending upon wavelength.

Under certain circumstances, and particularly at low saturation levels, the non-invasive pulse oximetry arterial oxygen saturation estimate, i.e. $SpO_2$, may be strongly affected by parameters other than the actual saturation level (i.e., $SaO_2$). Such effects are likely due, at least in part, to the fact that the penetration of light in living tissue is related to the wavelength-dependent absorption and scattering characteristics of the tissue, and that therefore two different wavelengths of light in the ranges typically employed for pulse oximetry penetrate such tissue to different extents. At high blood oxygen saturation levels the difference in extent of light penetration is relatively small and there is little effect on $SpO_2$. However, as saturation levels decrease, the difference in penetration can become great enough so that these other parameters have a significant and undesirable effect on the accuracy of $SpO_2$.

For example, in oximetry systems which employ LEDs having wavelengths of 660 and 900 nm with the sensor configured in a "reflectance" geometry, as the saturation level drops, light from the red LED (660 nm) is detected from relatively shallow tissue depths, while light from the infrared LED (900 nm) typically penetrates the tissue more deeply. This phenomenon may be understood with reference to FIG. 1. As the penetration depths diverge it becomes apparent that the different wavelengths will encounter increasingly different transmission medium characteristics. As a result, the detected signals are affected differently by perturbations in tissue parameters caused by, for example, vasoconstriction or exsanguination in the superficial layers. Because the detected signals encounter different perturbations, the effects of these perturbations in the two signals do not "cancel" each other out to the same extent as in circumstances in which the penetration depths are well matched. Consequently, the accuracy of $SpO_2$ may be negatively affected.

Figure 2:
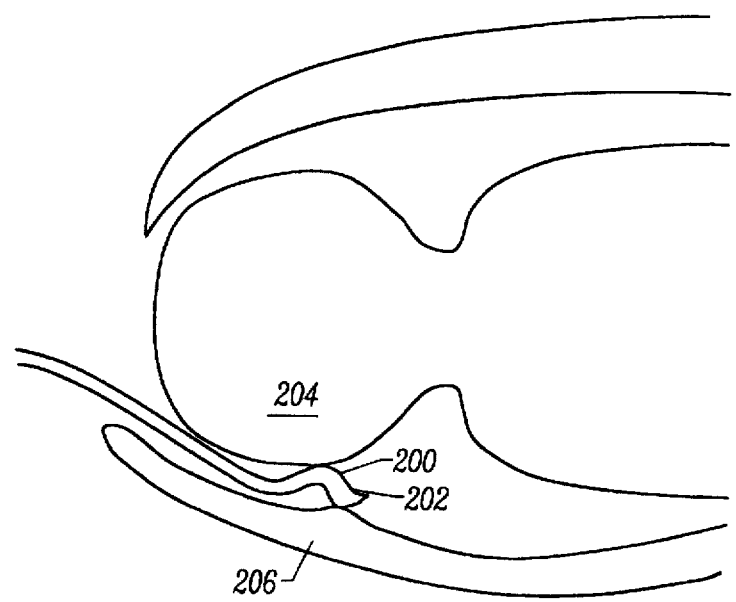
FIG. 2 is a diagram illustrating a fetal sensor biased against a fetus.

FIG. 2 illustrates a sensor 200 with a fulcrum point 202 biasing sensor 200 against the head of a fetus 204 by pressing against a uterine wall 206. The need to press the sensor against the fetus to hold it in place may also exsanguinate the tissue, potentially causing a portion of it to be bloodless, adding a different variation in the tissue through which the light must scatter.

Figure 3:
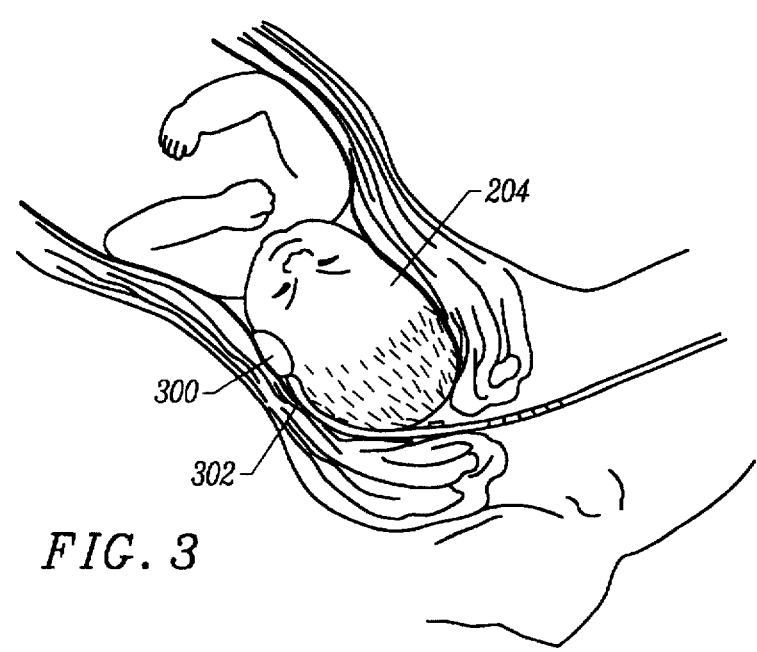
FIG. 3 is a diagram illustrating the insertion of a fetal sensor into a uterus.

FIG. 3 illustrates in more detail how an alternate fetal sensor may be placed against a fetus 204. As shown here, a fetal sensor 300 is attached to a stiff cable 302 which allows it to be inserted and placed against the fetus 204. Rather than using a fulcrum, sensor 300 may use a balloon to bias the sensor against the fetus.

FIG. 4 illustrates in more detail emitter 114 of FIG. 1. The emitter actually contains three separate emitters 402, 404 and 406. These are each connected between a ground line 408 and three activating lines 410 (shown as one line in the diagram.)

FIG. 5 is a block diagram of an oximeter probe and monitor which can be used with the present invention. A complete description is set forth in U.S. Pat. No. 5,348,004. LEDs 14 transmit light through patient tissue 18 to a photosensor 16 in a sensor 10. Signals are provided to and from an oximeter monitor 34 which include an LED drive 32 for alternately driving the LEDs in multiplexed fashion, either time multiplexed or frequency multiplexed. The received signals are provided through an input amplifier 20 to three different oversampling demodulators 36 which each include an analog switch 40, low pass filter 42 and A/D converter 38. A processing unit 44 includes a queue input module 46, RAM memory 52 and CPU 50. A readout display 30 is also provided, along with control lines 68. The memory may alternately be ROM or a disk, which may contain a program for performing the calculations of the present invention.

A calibration resistor (or other active or passive element) 17 encodes the mean wavelength of at least one LED, and provides it to a calibration reader circuit 19, which provides it to CPU 50. The wavelength indicated is used to select coefficients stored in monitor 34. Such a calibration technique is described in more detail in U.S. Pat. No. 4,621,643, the disclosure of which is incorporated herein by reference.

Saturation Calculation

In order to compensate for errors resulting from a single estimate of $SpO_2$, a second measurement is conducted at substantially the same time and location in a different manner which has a different, but correlated, susceptibility to the perturbing influence. A first measurement of saturation is performed using a first group of components of the sensor. The value obtained, $M_1$ is equal to the true saturation $SaO_2$ plus some error referred to here as $\delta$:

$$M_1 = SaO_2 + \delta. \quad (1)$$

The error $\delta$ can come from a number of different causes but is considered here to describe the sensitivities of the measurement to parameters other than $SaO_2$. At substantially the same time as the first measurement, and at the same location, a second measurement $M_2$ is performed using a second group of components of the sensor. The second group of components is selected so that the second measurement has a different sensitivity to the perturbing factors than the first measurement, but nonetheless is still sensitive to the cause of the perturbation. As a result, the value $M_2$ can be written:

$$M_2 = SaO_2 + K\delta, \quad (2)$$

where K represents the ratio of error in the $SpO_2$ measurement present in $M_2$ to that present in $M_1$, and may be approximated by a constant. K is, to a useful approximation, only a function of the physical sensor design (constraints on K are that K≠0 and K≠1.) The variation in error, as the sensor is used on different tissue sites, on different patients, or at different times, or as other physiological parameters vary, appears primarily in variations in the magnitude of δ, and only to a significantly smaller extent in the value of K. Accordingly, an improved estimate of oxygen saturation ($M_3$) is attained by solving Equations (1) and (2) for $SaO_2$:

$$SaO_2(=M_3)=\{K/(K-1)\}M_1+\{1/(1-K)\}M_2. \quad (3)$$

Notice that $M_3$ is not subject to the perturbation δ. Realistically $M_3$ will have residual sensitivity to δ, but will nonetheless be less sensitive to the perturbation than either $M_1$ or $M_2$ because of their correlated sensitivities. The functional relationship of the perturbation-free value $M_3$ to the measured values $M_1$ and $M_2$, and the coefficients used, would be empirically determined in a calibration process during instrument design.

One cause of limited $SpO_2$ accuracy is an imbalance in penetration depths of the detected light at two wavelengths. Accordingly, a three-wavelength sensor can compensate for the resulting errors. The degree of error in a two-wavelength (2–λ) oximeter will relate to the degree of mismatch in detected light penetration. At low saturation, an error in $SpO_2$ observed with, for example, a 660/900 nm light sensor is worse than the error that comes from a 735/900 nm light sensor under the same conditions, as described above. Such errors, however, can be expected to be correlated since light penetration is smoothly distributed over a broad range, with significant overlap even when each different wavelength has a different average penetration depth. Following the methodology described above, the correlation of the $SpO_2$ "errors" can be used to compute a revised (or "corrected") estimate of $SpO_2$ based on the difference of the two 2–λ sensors' values:

$$SpO_2{}^{corrected}=[SpO_2]^{735/900}+k([SpO_2]^{735/900}-[SpO_2]^{660/900}). \quad (4)$$

Here, $[SpO_2]^{735/900}$ and $[SpO_2]^{660/900}$ refer to the conventionally computed saturations using 735 nm and 900 nm, or 660 nm and 900 nm wavelength pairs, respectively, while k is a proportionality constant. It should be recognized that equation (4) can be mathematically transformed in a variety of ways that result in fundamentally the same calculations. For example, the improved estimate of $SpO_2{}^{corrected}$ can be equivalently determined without specific intermediate calculations or determinations of the two 2–λ estimates of $SpO_2$ by replacing these values with their respective formulations based on their measured signal intensities. This will become more clear as the invention is further described below.

In a preferred embodiment, the sensor is fabricated with three light emitting diodes and a spaced photodetector. The three LEDs are located as close to one another as possible so as best to illuminate the same region of tissue. $SpO_2$ is calculated for each of the two red/IR combinations independently, following normal pulse oximetry protocols as known to those skilled in the art. The revised estimate of $SpO_2$ is made based on the difference between the two initial estimates according to equation (4) or its equivalent.

Figure 6:
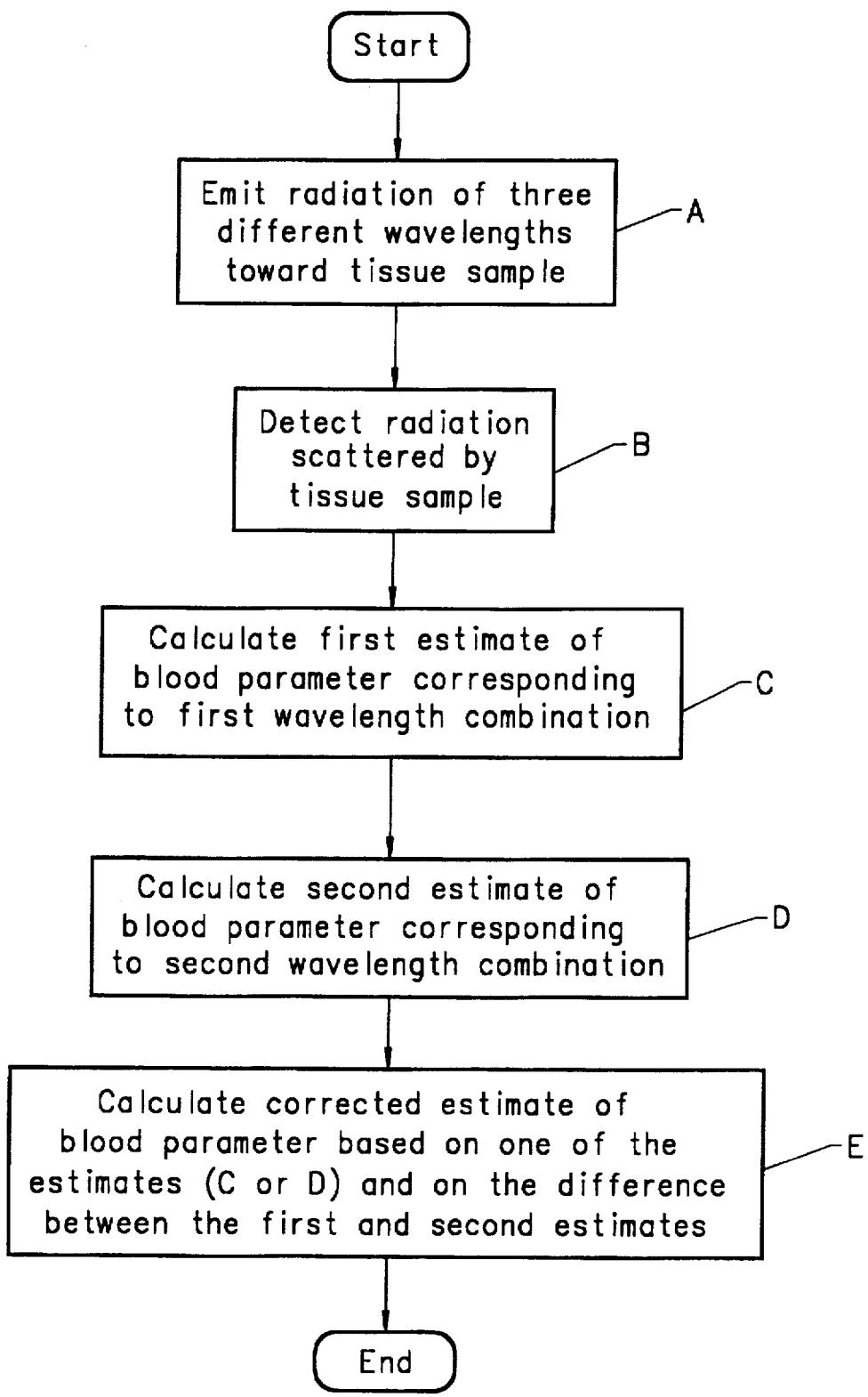
FIG. 6 is a flowchart illustrating the operation of an embodiment of the invention.

FIG. 6 is a flowchart illustrating the steps of the present invention. First, radiation of three different wavelengths is emitted towards the tissue sample (Step A.) In step B, the radiation scattered by the tissue sample is detected. In step C, a first estimate of a blood parameter (e.g., arterial oxygen saturation) corresponding to a first pair of wavelengths is determined. In step D, a second estimate of the blood parameter is determined according to a second pair of wavelengths. Finally, a corrected estimate is calculated based in part on the difference between the first and second estimates (Step E.) Alternately, the same result can be achieved by combining steps C, D and E to eliminate the intermediate calculations.

Wavelength Selection

Although the three wavelengths 660 nm, 735 nm, and 900 nm are utilized in the described preferred embodiment, other wavelengths may be selected, preferably according to the following table. Preferably, two wavelength pairs result in measurements of $SpO_2$ that have at least a minimum sensitivity to changes in $SaO_2$ (e.g., at least two wavelengths are chosen to be substantially different from the isosbestic wavelengths of oxygenated and deoxygenated hemoglobin). Simultaneously, two of the wavelengths should result in tissue penetrations of the detected light that are similar but not equivalent. The third wavelength is preferably chosen so that the degree of detected light penetration is not significantly different or substantially equivalent to either of the other two over the span of the saturation range of interest. It should be understood that typical light sources, such as LEDs, have relatively broad distributions of wavelengths in their output, and the ranges of wavelengths indicated in Table I below are ranges from which the peak wavelengths of the distributions should preferably be selected.

Accordingly, preferred wavelength combinations are chosen to meet the following two criteria evaluated at 40% $SaO_2$:

1) sufficient overlap in penetration of detected light between wavelengths 1 & 2 and wavelengths 2 & 3 (difference in upper, as well as lower, half standard deviation penetration depths less than 2 mm and not less than 0.2 mm), and 2) sufficient measurement sensitivity to changes in $SaO_2$ for wavelength pairs 1 & 3 and 2 & 3 (sufficient sensitivity determined by R[0% $SaO_2$]>2·R [100% $SaO_2$], where R=$\beta_\lambda/\beta_{\lambda'}$ and $\beta_\lambda$ refers to the extinction coefficient at wavelength λ.)

Table I below was calculated utilizing the formulations for the average and standard deviation in detected light penetration found in Weiss et al., "Statistics of penetration depth of photons re-emitted from irradiated tissue," Journal of Modern Optics, vol. 36, no. 3, 1989. For convenience, wavelength 1 is listed in 25 nm increments, and it should be noted that according to the above selection criteria, wavelengths 1 and 2 (and in some cases all three wavelengths) are interchangeable. In the table below, each row represents combinations of peak emitter wavelengths that satisfy the preferred selection criteria (all wavelengths given in nanometers):

TABLE I

| Wavelength 1 (± 12.5 nm) | Wavelength 2* | Wavelength 3* |
|---|---|---|
| 450 | 450–525 | 600–700 |
| 475 | 525–675 | 500–825 |
| 500 | 525–675 | 575–775 |
| 525 | 575–675 | 575–775 |
| 550 | 475–525 | 600–675 |
|  | 575–650 | 450–775 |
| 575 | 475–500 | 600–675 |
|  | 550–675 | 600–775 |
| 600 | 450–600 | 625–675 |
|  | 600–675 | 450–600 |

TABLE I-continued

| Wavelength 1 (± 12.5 nm) | Wavelength 2* | Wavelength 3* |
|---|---|---|
|  | 600–675 | 775–950 |
| 625 | 650–800 | 725–950 |
|  | 775–925 | 725–775 |
| 650 | 600–625 | 450–600 |
|  | 675–800 | 775–950 |
|  | 775–950 | 700–775 |
| 675 | 600–650 | 450–600 |
|  | 600–650 | 725–950 |
|  | 700–800 | 775–950 |
|  | 775–950 | 700–800 |
| 700 | 600–675 | 450–600 |
|  | 600–675 | 725–950 |
|  | 775–950 | 725–775 |
| 725,750 | 600–700 | 450–600 |
|  | 600–700 | 775–950 |
|  | 775–950 | 625–700 |
| 775 | 600–700 | 450–600 |
|  | 600–700 | 800–950 |
|  | 800–950 | 625–725 |
| 800, 825, 850, 900 | 625–700 | 600–775 |
|  | 700–775 | 625–700 |

*Wavelengths chosen from overlapping ranges should be separated by at least 10 nm, preferably at least 30 nm, from one another.

For a system designed to be practical in a clinical setting, other considerations will also affect the choice of emitter wavelengths such as emitter output efficiency, detector responsivity, and the optical density of blood perfused tissues at the given wavelengths. Table I optimizes only the overlap criterion and the measurement sensitivity for a three wavelength system which considers a common ratiometric denominator (wavelengths 1 and 3 are used for one $SpO_2$ estimation and wavelengths 2 and 3 are used for a second.) Similar optimizations can also be accomplished for variations of the $SpO_2$ formulations. For example, wavelengths 1 and 2 can be used for one $SpO_2$ estimation and 2 and 3 can be used for a second. In such a case, the sensitivity optimization would pair wavelengths 1 & 2 and 2 & 3, instead of the pairings considered in generating Table I. Alternative light penetration overlapping schemes may be considered as well.

Detailed Description of Algorithms

Described more fully, the following algorithm is used in the preferred embodiment. Light at three wavelengths is provided at the emitter location using three LEDs or other suitable source (for example delivered with an optical fiber). In order to optimize sensitivity and overlap according to the above wavelength selection criteria, as well as detected signal strength (affected by, for example, emitter output and the optical density of blood perfused tissue), three emitter wavelengths are chosen with two coming from the range 625–800 nm, preferably 650–750 nm, and the third from 775–1000 nm. The peak of each emitter wavelength should be separated by at least 10 nm, preferably at least 30 nm, from the other wavelengths; however, other combinations, ranges, and separations may be used while still conforming to the spirit of the invention.

Three emitters may be sequentially energized in a time multiplexed manner as described in U.S. Pat. No. 4,653,498 (New & Corenman), or in a frequency multiplexed manner as in U.S. Pat. No. 4,807,630 (Malinouskas). Alternatively, either three continuously operating sources or white light may be used, with the different wavelength ranges being separated at the photodetector with filters or a dispersive element. In this latter case, separate photodetector cells will be needed for each of the three different wavelength ranges of light. For the time multiplexed systems, the cycle frequency should be chosen to permit cycling through all of the three or more wavelengths before significant physiological variation occurs over the cardiac-cycle period. For example, it would usually be sufficient for each complete wavelength cycle to occur within 5% of a cardiac period, or about 50 ms for adult patients. A more preferred time multiplexing period would be 2% or less of a cardiac period, which is to say 20 ms or less for adult patients and 10 ms or less for neonatal patients.

Detected signals at the three wavelengths are processed to obtain three signal modulation levels:

$$m_1 = \log(I(t)/I(t'))|_{\lambda_1} \approx (AC/DC)|_{\lambda_1} \quad (e.g., \lambda_1=660 \text{ nm}) \tag{5a}$$

$$m_2 = \log(I(t)/I(t'))|_{\lambda_2} \approx (AC/DC)|_{\lambda_2} \quad (e.g., \lambda_2=735 \text{ nm}) \tag{5b}$$

$$m_3 = \log(I(t)/I(t'))|_{\lambda_3} \approx (AC/DC)|_{\lambda_3} \quad (e.g., \lambda_3=900 \text{ nm}) \tag{5c}$$

where I(t) and I(t') are the detected light intensities at two points in time during the cardiac cycle (e.g., systolic and diastolic). The logarithmic calculations above, which fundamentally define the signal modulations $m_1$ through $m_3$, may be approximated for sufficiently small modulations by the ratio of the AC signal amplitude divided by the DC signal amplitude, since this approximates the first term of a Taylor expansion of $\log(1+x)$, when x is small. Two of the signal modulation values $m_1$, $m_2$ are divided by the third modulation value $m_3$ to obtain two ratios. Two $SpO_2$ values are calculated according to prior art methods (a linear formula is shown here and is used in the preferred embodiment, but other formulae may be alternatively used):

$$R_1 = \frac{m_1}{m_3}; \quad SpO_2(1) = a_1 R_1 + b_1 \tag{6a}$$

$$R_2 = \frac{m_2}{m_3}; \quad SpO_2(2) = a_2 R_2 + b_2 \tag{6b}$$

where $a_1$, $a_2$, $b_1$ and $b_2$ are empirically determined calibration coefficients selected by the usual methods of pulse oximetry calibration. Alternative calculations to create two Ratios using these or other chosen wavelengths are also possible, e.g., $m_1/m_2$ and $m_1/m_3$ or $m_1/m_2$ and $m_2/m_3$. Calculations of the two Ratios or $SpO_2$ values that do not specifically utilize signals at only two specific points in the cardiac cycle can alternatively be used, for example as described in U.S. Pat. No. 5,533,507.

Once the two $SpO_2$ values have been calculated, an improved estimate of $SpO_2$ is made according to the difference in the initial estimates:

$$\Delta \equiv SpO_2(2) - SpO_2(1) \tag{7}$$

$$SpO_2(\text{improved}) \equiv SpO_2(2) + k \cdot \Delta \tag{8a}$$

The correlation factor 'k' can be estimated theoretically, but is preferably determined empirically.

By way of example, each of the following equations is mathematically equivalent to equation (8a), yet not all of them necessarily require intermediate calculations of $SpO_2(1)$ and $SpO_2(2)$:

$$SpO_2 \text{ (improved)} = (1 + k) \cdot SpO_2(1) + (-k) \cdot SpO_2(2) \tag{8b}$$

$$SpO_2 \text{ (improved)} = A \cdot R_1 + B \cdot R_2 + C \tag{8c}$$

$$SpO_2 \text{ (improved)} = \frac{1}{m_3} \cdot (A \cdot m_1 + B \cdot m_2) + C \tag{8d}$$

$$SpO_2 \text{ (improved)} = \frac{DC_3(A \cdot AC_1DC_2 + B \cdot AC_2DC_1)}{AC_3DC_1DC_2} + C \qquad (8e)$$

where $A=a_1(1+k)$; $B=-ka_2$; $C=[b_1(1+k)-b_2k]$. Equation (8e) could also be rewritten by substituting $\log(I(t)/I(t'))$ for the AC/DC terms, in accordance with equations (5a), (5b), and (5c).

It is also possible to establish general equations for solutions of this type, which can be written as follows, for N wavelengths ($N \geq 3$):

$$SpO_2(\text{improved}) = \sum_{i=1}^{N-1} a_i(SpO_2)_i \qquad (9a)$$

$$= \sum_{i=1}^{N-1} (\alpha_i R_i) + \beta \qquad (9b)$$

$$= \frac{1}{m_N} \cdot \sum_{i=1}^{N-1} \alpha_i m_i + C \qquad (9c)$$

($m_x$ is the modulation amplitude at $\lambda_x$)

$$= \frac{DC_N}{AC_N} \cdot \sum_{i=1}^{N-1} \alpha_i \frac{AC_i}{DC_i} + C \qquad (9d)$$

The alternative (but not mathematically equivalent) calculations of the modulation ratios mentioned above can be written in general form for N wavelengths ($N \geq 3$) as $$SpO_2(\text{improved}) = m_1 \cdot \sum_{i=2}^{N} \frac{\alpha_i}{m_i} + C, \qquad (10a)$$

or $$SpO_2(\text{improved}) = \sum_{i=2}^{N} \alpha_i \frac{m_{i-1}}{m_i} + C. \qquad (10b)$$

For N>3 wavelengths, various combinations of (9c), (10a), and (10b) are also possible and are considered to be within the scope of the invention to the extent that they mathematically relate to combining multiple determinations of $SpO_2$.

The different embodiments of the method of the invention outlined here are specifically different from prior art pulse oximeter techniques in one or more of the following ways:

1) The errors from many potential causes (more than two) are compensated for by the use of as few as three wavelengths, as opposed to supplying the same or more numbers of wavelengths as causes (e.g., one each wavelength for the number of functional and dysfunctional hemoglobins potentially present).

2) Tissues are not assumed to be homogeneous in the percentage of tissue volume which is blood, distribution of pulsatile vessels or of other non-absorbing and absorbing media, and resulting $SpO_2$ readings are less affected by such heterogeneity than they would be in a standard two-wavelength pulse oximeter.

3) The specific perturbations to which the system will be exposed during use do not need to be present during the calibration.

4) No information other than $SpO_2$ is determined during the calculations, such as whether a given sample is within certain boundaries defined by the calibration data set, or the concentration or saturation of any additional absorbers in the tissue.

5) Arterial oxygen saturation is estimated with improved accuracy under conditions when light penetration into the tissues cannot be sufficiently matched for adequate accuracy with conventional two wavelength oximeters.

6) For the multiple calculations of saturation, all of the light is directed into the tissue at one emitter area and all of the detected light is collected in one detector area.

Figures 7A, 7B:
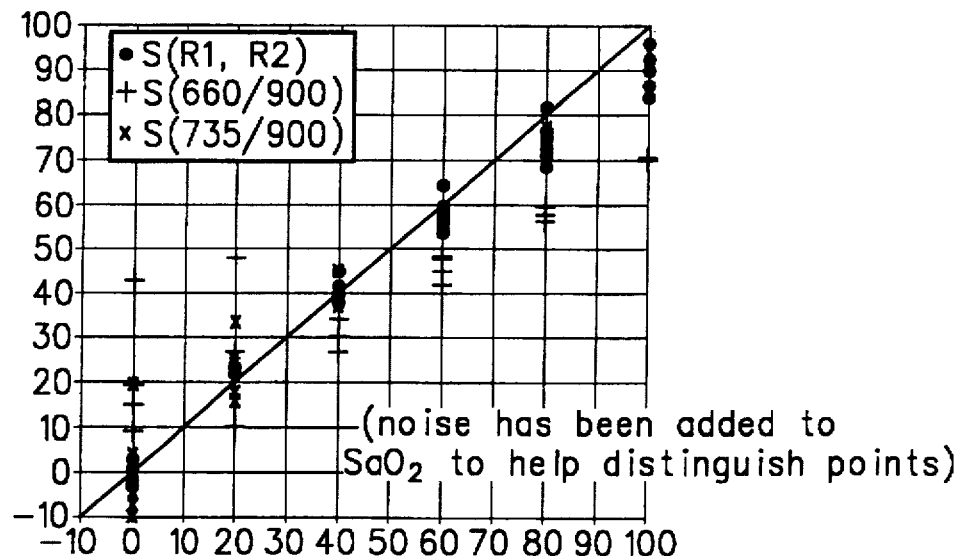
FIG. 7A–7B are a chart and table illustrating the different errors for prior art two wavelength oximeters and the present invention.

Numerical Modeling Numerical modeling has been performed to evaluate theoretically the relative behavior of two conventional 2–$\lambda$ and the new 3–$\lambda$ approaches. Reflectance pulse oximetry was considered and various one- and two-layer tissue bed systems were modeled with the emitter and detector separated by 14 mm. Varying tissue blood volumes, pulsatility, and layer thickness were considered. Shown in FIGS. 7A and 7B are the relative performances of two 2–$\lambda$ systems (660/900 nm and 735/900 nm), and the revised 3–$\lambda$ estimate using a linear proportionality and fixed 'k' value as in equation (4). Data from six types of tissue beds are shown: homogenous distributions of low, moderate and high tissue blood content; 3 mm layer of low pulsatility tissue over large pulsatility tissue; 3 mm layer of large pulsatility over low pulsatility tissue; and 3 mm layer of completely bloodless tissue over moderately perfused tissue. All three approaches were optimized (calibrated) to yield the minimum least-squares error in the saturation range 0%–60%. In the example shown here, the heterogeneous perturbations were present during calibration. Similar results are obtained for the improved algorithm when the calibration is performed using only the homogeneous conditions. As can be seen in the FIG. 7A graph of $SpO_2$ versus $SaO_2$, the improved algorithm results in significantly less sensitivity to the modeled homogenous and heterogeneous perturbations at low saturation. The table shows the standard deviation of the errors in the low saturation range for the three systems, as well as the range of readings at 20% $SaO_2$. Although not shown, similar results are observed in the improved algorithm when a 690 nm emitter is used instead of 735 nm emitter.

Further Improvements

Variations in equation (4) can also be utilized, e.g., incorporating the difference term in a non-linear relationship such as a higher order polynomial or power-law:

$$SpO_2(\text{improved})=SpO_2(2)+k_1 \cdot \Delta+k_2 \cdot \Delta^2+\ldots \qquad (11)$$

$$SpO_2(\text{improved})=SpO_2(2)+k \cdot \Delta^p \qquad (12)$$

Further improvements may be realized by varying the value of 'k' according to a predetermined set of rules. For example, the value of 'k' may depend on the calculated $SpO_2$ difference $\Delta$:

$$k = \begin{cases} k_1 & \Delta < \Delta_0 \\ k_2 & \Delta_0 \leq \Delta < \Delta_1 \\ k_3 & \Delta \geq \Delta_1 \end{cases} \qquad (13)$$

The values of '$k_j$' and of the thresholds $\Delta_0$ and $\Delta_1$ may be empirically determined. Alternatively, the value of 'k' may be varied based on an estimate of saturation. For example, 'k' need not be as large at high saturations as it is at low saturations:

$$k = \begin{cases} k_1 & SpO_{2est} < S_0 \\ k_2 & S_0 \leq SpO_{2est} < S_1, \\ k_3 & SpO_{2est} \geq S_1 \end{cases} \quad \text{or } k = f(SpO_{2est}) \qquad (14)$$

where $SpO_{2est}$ may be the improved $SpO_2$ previously calculated, or one of the intermediate values determined from one or both of the wavelength pairs. (As was shown above, algebraic equivalence to each of these variations is possible when the individual signals or intermediate calculations are substituted into the above equations. Thus, in the spirit of these examples showing the use of variable k, it is also possible to write variants of the formulae of equations (8) and (9), in which the coefficients utilized are given different values depending on the values of an initial estimate of $SpO_2$.)

Any three wavelengths may be utilized with this algorithm while still following the spirit of the present invention. The concept exploits the correlated errors based on any two wavelengths' mismatched penetration depths and/or breadths. (For example, comparable improvement was also modeled using 660/690/900 nm wavelengths using a different value of 'k' in equation (4).) Alternatively, four or more wavelengths could be utilized according to the present invention with the two intermediate estimates of $SpO_2$ each made with two unique subsets of the four or more wavelengths (3–λ $SpO_2$ estimates could be made according to the present invention, or any of the prior-art techniques).

The use of more than a minimum of three wavelengths can be utilized for calculations isolating more than $SaO_2$. Constituents other than arterial blood oxygen saturation (e.g., hemoglobin, dysfunctional hemoglobin, or glucose) may be analyzed using the present invention. similarly, non-pulsatile signals may be used to initially estimate a variable, and a subsequent improved estimate may be obtained using the described algorithm. To the extent that any multiple wavelength system is limited in its accuracy (due to, e.g., mismatching light penetration), making an additional estimate based on a different set of wavelengths with different interaction with tissue properties yields a different value with a correlated error. This error may be corrected, as described above, by utilizing further the difference of the estimates, or an algebraically equivalent calculation.

As will be understood by those of skill in the art, the present invention may be embodied in other specific forms without departing from the spirit or essential characteristics thereof. Accordingly, the foregoing description is intended to be illustrative, but not limiting, of the scope of the invention which is set forth in the following claims.

What is claimed is:

1. A method for determining a blood constituent comprising the steps of:

emitting electromagnetic radiation of at least three wavelengths toward a patient;

detecting a portion of the electromagnetic radiation scattered by the tissue of said patient for each of said at least three wavelengths and generating at least three signals indicative thereof;

determining a blood constituent result from a combination of said at least three signals, said result being equivalent to the sum of (1) a first blood constituent estimate determined using a first set of at least two of said signals and (2) a multiplicative factor multiplied by a difference between said first blood constituent estimate and a second blood constituent estimate, said second blood constituent estimate being determined using a second set of a different combination of at least two of said signals.

2. The method of claim 1 wherein said result is determined utilizing a formula of the form $M=M(1)+k \cdot [M(1)-M(2)]^p$, wherein $M(1)$ is determined utilizing a set of signals comprising at least 2 wavelengths and $M(2)$ is determined utilizing a different set of signals comprising at least 2 wavelengths that are not all equal to the first set, k is a multiplicative factor and p is a exponential factor.

3. The method of claim 1 wherein said result is determined utilizing a formula of the form $M=aR_1+bR_2+c$, wherein $R_1$ is determined utilizing a set of signals comprising at least 2 wavelengths and $R_2$ is determined utilizing a different set of signals comprising at least 2 wavelengths that are not all equal to the first set, and a, b, and c are constants.

4. The method of claim 1 wherein said result is determined utilizing a formula of the form $M=(1/m_3)(am_1+bm_2)+c$, where $m_1$, $m_2$, and $m_3$ are signal modulation amplitudes emanating from a cardiac pulse determined at 3 different wavelengths, and a, b, and c are constants.

5. The method of claim 1 wherein said result is determined utilizing a formula of the form $M=m_3(a/m_1+b/m_2)+c$, where $m_1$, $m_2$, and $m_3$ are signal modulation amplitudes emanating from a cardiac pulse determined at 3 different wavelengths, and a, b, and c are constants.

6. The method of claim 1 wherein said result is determined utilizing a formula of the form $M=M(1)+f(\Delta)$, wherein f is a polynomial function, $\Delta$ is the difference between two blood constituent estimates from different wavelength combinations and $M(1)$ is determined utilizing a set of signals comprising at least 2 wavelengths.

7. The method of any one of claims 1–6 wherein said blood constituent is arterial oxygen saturation.

8. The method of claim 1 wherein said multiplicative factor is a function of at least one of said blood constituent estimates.

9. The method of claim 1 wherein said result is determined utilizing said three signals in a bivariate formula, having two variables, said variables being said first and second blood constituent estimates.

10. A method for determining a blood constituent comprising the steps of:

emitting electromagnetic radiation of at least three wavelengths toward a patient;

detecting a portion of the electromagnetic radiation scattered by the tissue of said patient for each of said at least three wavelengths and generating at least three signals indicative thereof;

determining a blood constituent result utilizing at least one coefficient chosen to compensate for variations in detected radiation paths through said patient of said electromagnetic radiation for at least two of said wavelengths.

11. The method of claim 10 further comprising the step of multiplexing said three wavelengths in said emitting step.

12. The method of claim 11 wherein said multiplexing is time multiplexing.

13. The method of claim 11 wherein said multiplexing is frequency multiplexing.

14. A method for determining a blood constituent comprising the steps of:

emitting electromagnetic radiation of at least three wavelengths toward a patient;

detecting a portion of the electromagnetic radiation scattered by the tissue of said patient for each of said at least three wavelengths and generating at least three signals indicative thereof;

determining a blood constituent result utilizing said at least three signals; and wherein said at least three wavelengths are chosen so that (1) first and second groups of said wavelengths have sufficient sensitivity to changes in said blood constituent so that a ratio of detected values varies by more than double between 0 and 100 percent of said blood constituent, and (2) said first and second groups of wavelengths have different penetrations into said patient with sufficient overlap to provide correlated errors in blood constituent calculations using said first and second groups of wavelengths.

15. The method of claim 14 wherein said wavelengths are chosen from among the groupings set forth in Table 1 herein.

16. The method of claim 14 wherein said wavelengths include at least one wavelength between 625–800 nm. and at least one wavelength between 775–1000 nm.

17. The method of claim 14 wherein said wavelengths include at least two wavelengths between 650–750 nm. and at least one wavelength between 775–1000 nm.

18. The method of claim 14 wherein said wavelengths are separated by at least 10 nm.

19. The method of claim 14 wherein said wavelengths are separated by at least 30 nm.

20. The method of claim 14 wherein said blood constituent is arterial oxygen saturation.

21. The method of claim 14 further comprising the step of multiplexing said three wavelengths in said emitting step.

22. The method of claim 14 further comprising the step of selecting, based on an encoded value from a sensor, coefficients for use in calculating said blood constituent.

23. An apparatus for determining a blood constituent comprising:
  at least one emitter configured to emit electromagnetic radiation of at least three wavelengths toward a patient;
  a detector configured to detect a portion of the electromagnetic radiation scattered by the tissue of said patient for each of said at least three wavelengths and generating at least three signals indicative thereof;
  means for determining a blood constituent result from a combination of said at least three signals, said result being equivalent to the sum of (1) a first blood constituent estimate determined using a first set of at least two of said signals and (2) a multiplicative factor multiplied by a difference between said first blood constituent estimate and a second blood constituent estimate, said second blood constituent estimate being determined using a second set of a different combination of at least two of said signals.

24. The apparatus of claim 23 wherein said result is determined utilizing a formula of the form $M=M(1)+k \cdot [M(1)-M(2)]^p$, wherein $M(1)$ is determined utilizing a set of signals comprising at least 2 wavelengths and $M(2)$ is determined utilizing a different set of signals comprising at least 2 wavelengths that are not all equal to the first set, k is a multiplicative factor and p is a exponential factor.

25. The apparatus of claim 24 wherein said result is determined utilizing a formula of the form $M=m_3(a/m_1+b/m_2)+c$, where $m_1$, $m_2$, and $m_3$ are signal modulation amplitudes emanating from a cardiac pulse determined at 3 different wavelengths, and a, b, and c are constants.

26. The apparatus of claim 23 wherein said result is determined utilizing a formula of the form $M=aR_1+bR_2+c$, wherein $R_1$ is determined utilizing a set of signals comprising at least 2 wavelengths and $R_2$ is determined utilizing a different set of signals comprising at least 2 wavelengths that are not all equal to the first set, and a, b, and c are constants.

27. The apparatus of claim 23 wherein said result is determined utilizing a formula of the form $M=(1/m_3)(am_1+bm_2)+c$, where $m_1$, $m_2$, and $m_3$ are signal modulation amplitudes emanating from a cardiac pulse determined at 3 different wavelengths, and a, b, and c are constants.

28. The apparatus of claim 23 wherein said result is determined utilizing a formula of the form $M=M(1)+f(\Delta)$, wherein f is a polynomial function, $\Delta$ is the difference between two M estimates from different waveform combinations, and $M(1)$ is determined utilizing a set of signals comprising at least 2 wavelengths.

29. The apparatus of any of claims 23–28 wherein said blood constituent is arterial oxygen saturation.

30. The apparatus of claim 23 wherein said multiplicative factor is a function of at least one of said blood constituent estimates.

31. The apparatus of claim 23 wherein said result is determined utilizing a bivariate formula, having three wavelengths and two variables, said variables being said first and second blood constituent estimates.

32. An apparatus for determining a blood constituent comprising:
  means for emitting electromagnetic radiation of at least three wavelengths toward a patient;
  means for detecting a portion of the electromagnetic radiation scattered by the tissue of said patient for each of said at least three wavelengths and generating at least three signals indicative thereof;
  means for determining a blood constituent result utilizing at least one coefficient chosen to compensate for variations in detected radiation paths through said patient of said electromagnetic radiation for at least two of said wavelengths.

33. The apparatus of claim 32 further means for emitting and detecting comprise a sensor, and further comprising means for biasing said sensor against a fetus.

34. The apparatus of claim 32 further comprising means for multiplexing said three wavelengths in said means for emitting.

35. The apparatus of claim 23 wherein said blood constituent is arterial oxygen saturation.

36. An apparatus for determining a blood constituent comprising:
  means for emitting electromagnetic radiation of at least three wavelengths toward a patient;
  means for detecting a portion of the electromagnetic radiation scattered by the tissue of said patient for each of said at least three wavelengths and generating at least three signals indicative thereof;
  means for determining a blood constituent result utilizing said at least three signals; and
  wherein said at least three wavelengths are chosen so that
    (1) first and second groups of said wavelengths have sufficient sensitivity to changes in said blood constituent so that a ratio of detected values varies by more than double between 0 and 100 percent of said blood constituent, and
    (2) said first and second pairs of wavelengths have different penetrations of said patient with sufficient overlap to provide correlated errors in blood constituent calculations using said first and second groups of wavelengths.

37. The apparatus of claim 36 wherein said wavelengths are chosen from among the groupings set forth in Table 1 herein.

38. The apparatus of claim 36 wherein said wavelengths include at least one wavelength between 625–800 nm. and at least one wavelength between 775–1000 nm.

39. The apparatus of claim 36 wherein said wavelengths are separated by at least 10 nm.

40. The apparatus of claim 36 wherein said wavelengths are separated by at least 30 nm.

41. The apparatus of claim 36 wherein said blood constituent is arterial oxygen saturation.

42. An oximeter processor comprising:
  means for receiving, as an input, signals corresponding to a portion of electromagnetic radiation scattered by the tissue of a patient for each of at least three wavelengths of electromagnetic radiation directed toward a patient; and
  means for determining a blood constituent result from a combination of said at least three signals, said result being equivalent to the sum of (1) a first blood constituent estimate determined using a first set of at least two of said signals and (2) a multiplicative factor multiplied by a difference between said first blood constituent estimate and a second blood constituent estimate, said second blood constituent estimate being determined using a second set of a different combination of at least two of said signals.

43. The monitor of claim 42 wherein said result is determined utilizing a formula of the form $M=M(1)+f(\Delta)$ wherein f is a polynomial function and $\Delta$ is the difference between two blood constituent estimates from different waveform combinations.

44. The monitor of claim 42 wherein said blood constituent is arterial oxygen saturation.

45. An oximeter processor comprising:

means for receiving as an input signals corresponding to a portion of electromagnetic radiation scattered by the tissue of a patient for each of at least three wavelengths of electromagnetic radiation directed toward a patient; and means for determining a blood constituent result utilizing at least one coefficient chosen to compensate for variations in path lengths through said patient of said electromagnetic radiation for at least two of said wavelengths.

46. The monitor of claim 45 wherein said blood constituent is arterial oxygen saturation.

47. A software program product comprising:

a memory having a program stored thereon, said program being usable by a processing device, said program being configured to receive, as an input, signals corresponding to a portion of the electromagnetic radiation scattered by the tissue of a patient for each of at least three wavelengths of electromagnetic radiation directed toward a patient; and determine a blood constituent result from a combination of said signals, said result being equivalent to the sum of (1) a first blood constituent estimate determined using a first set of at least two of said signals and (2) a multiplicative factor multiplied by a difference between said first blood constituent estimate and a second blood constituent estimate, said second blood constituent estimate being determined using a second set of a different combination of at least two of said signals.

48. The product of claim 47 wherein said result is determined utilizing a formula of the form $M=M(1)+k \cdot [M(1)-M(2)]^p$, wherein M(1) is determined utilizing a set of signals comprising at least 2 wavelengths and M(2) is determined utilizing a different set of signals comprising at least 2 wavelengths that are not all equal to the first set, k is a multiplicative factor and p is a exponential factor.

49. The product of claim 47 wherein said result is determined utilizing a formula of the form $M=aR_1+bR_2+c$, wherein $R_1$ is determined utilizing a set of signals comprising at least 2 wavelengths and $R_2$ is determined utilizing a different set of signals comprising at least 2 wavelengths that are not all equal to the first set, and a, b, and c are constants.

50. The product of claim 47 wherein said result is determined utilizing a formula of the form $M=(1/m_3)(am_1+bm_2)+c$, where $m_1$, $m_2$, and $m_3$ are signal modulation amplitudes emanating from a cardiac pulse determined at 3 different wavelengths, and a, b, and c are constants.

51. The product of claim 47 wherein said result is determined utilizing a formula of the form $M=m_3(a/m_1+b/m_2)+c$, where $m_1$, $m_2$, and $m_3$ are signal modulation amplitudes emanating from a cardiac pulse determined at 3 different wavelengths, and a, b, and c are constants.

52. The product of claim 47 wherein said result is determined utilizing a formula of the form $M=M(1)+f(\Delta)$, wherein f is a polynomial function, $\Delta$ is the difference between two M estimates from different waveform combinations, and M(1) is determined utilizing a set of signals comprising at least 2 wavelengths.

53. The product of any of claims 47–52 wherein said blood constituent is arterial oxygen saturation.

54. The product of claim 47 wherein said multiplicative factor is a function of at least one of said blood constituent estimates.

55. The product of claim 47 wherein said result is determined utilizing a bivariate formula, having three wavelengths and two variables, said variables being said first and second blood constituent estimates.

56. A software program product comprising:

a memory having a program stored thereon, said program being usable by a processing device, said program being configured to receive as an input signals corresponding to a portion of the electromagnetic radiation scattered by the tissue of a patient for each of at least three wavelengths of electromagnetic radiation directed toward a patient; and determine a blood constituent result utilizing at least one coefficient chosen to compensate for variations in path lengths through said patient of said electromagnetic radiation for at least two of said wavelengths.

57. The product of claim 56 further comprising means for multiplexing said three wavelengths in said means for emitting.

58. The product of claim 56 wherein said blood constituent is arterial oxygen saturation.

* * * * *

UNITED STATES PATENT AND TRADEMARK OFFICE
CERTIFICATE OF CORRECTION

PATENT NO. : 5,782,756
DATED      : July 21, 1998
INVENTOR(S) : Paul D. Mannheimer It is certified that error appears in the above-identified patent and that said Letters Patent is hereby corrected as shown below:

In column 1, line 3, please insert the following:

--The United States Government has rights in the invention pursuant to Cooperative Research and Development Agreement TC-485-93 with Lawrence Livermore National Laboratory.--

Signed and Sealed this

Seventh Day of September, 1999

Attest:

Q. TODD DICKINSON

*Attesting Officer*    *Acting Commissioner of Patents and Trademarks*